United States Patent
Andrews et al.

[11] Patent Number: 5,935,501
[45] Date of Patent: *Aug. 10, 1999

[54] METHOD FOR MAKING A PACKAGING SHEATH FOR INTRA-AORTIC BALLOON CATHETERS

[75] Inventors: Robert R. Andrews, Norfolk; William Edelman, Sharon; Ilyssa A. Hunt, Tyngsboro, all of Mass.

[73] Assignee: Arrow International, Inc., Reading, Pa.

[ * ] Notice: This patent issued on a continued prosecution application filed under 37 CFR 1.53(d), and is subject to the twenty year patent term provisions of 35 U.S.C. 154(a)(2).

[21] Appl. No.: 08/483,923

[22] Filed: Jun. 7, 1995

Related U.S. Application Data

[62] Division of application No. 08/210,551, Mar. 18, 1994, Pat. No. 5,524,757.

[51] Int. Cl.⁶ .............................. B29C 33/12; B29C 45/14
[52] U.S. Cl. ....................... 264/250; 264/271.1; 264/295; 264/296
[58] Field of Search .................................... 264/250, 255, 264/257, 259, 271.1, 275, 294, 296, 295; 425/112, 577

[56] References Cited

U.S. PATENT DOCUMENTS

| | | | |
|---|---|---|---|
| 3,865,666 | 2/1975 | Shoney | 156/245 |
| 3,959,429 | 5/1976 | Benning | 264/263 |
| 4,582,092 | 4/1986 | Nissen | 138/109 |
| 4,801,015 | 1/1989 | Lubock et al. | 206/438 |
| 4,997,084 | 3/1991 | Opie et al. | 206/364 |
| 5,125,416 | 6/1992 | Phillips | 128/772 |
| 5,167,634 | 12/1992 | Corrigan, Jr. et al. | 604/160 |
| 5,262,113 | 11/1993 | Carmien | 264/257 |
| 5,343,861 | 9/1994 | Herman | 128/652 |
| 5,409,652 | 4/1995 | Carter | 264/263 |

FOREIGN PATENT DOCUMENTS

| | | |
|---|---|---|
| 0 228 787 | 7/1987 | European Pat. Off. . |
| 91/14473 | 10/1991 | WIPO . |

OTHER PUBLICATIONS

Photograph A—Cross–section of one end of prior sheath tube of St. Jude Medical, Inc.
Photographs B and C—Cross–sections of one end of prior sheath tubes of Datascope, Inc.

Primary Examiner—Angela Ortiz
Attorney, Agent, or Firm—Wolf, Greenfield & Sacks, P.C.

[57] ABSTRACT

An intra-aortic balloon packaging sheath is provided which includes a long slim extruded plastic tube for storing a furled thin-walled intra-aortic balloon. An entry section of the same plastic is injection molded onto one end of the tube, with the entry section including an outwardly flared entry port surface which is spaced from one end of the tube, and an internal passageway which is co-linear and congruent with the internal cross-section of the tube from the respective end of the tube through the intersection of the second internal passageway with the outwardly flared passageway. Thereby a smooth internal surface is provided through the flared passageway into the internal passageway and through the later into the tube. The exit end of the sheath tube is inverted by use of a heated tipping die such that a distal end portion is turned outwardly and back circumjacent another portion of the tube wall to form a smoothly rounded exit passageway of the tube at the exit end.

12 Claims, 2 Drawing Sheets

METHOD FOR MAKING A PACKAGING SHEATH FOR INTRA-AORTIC BALLOON CATHETERS

This is a divisional of application Ser. No. 08/210,551, filed on Mar. 18, 1994, now U.S. Pat. No. 5,524,757.

FIELD OF THE INVENTION

This invention relates to packaging sheaths for the balloon portion of intra-aortic balloon catheters. Such sheaths are used for the packaging of the furled balloon section of an intra-aortic balloon catheter (IABC) during the later stages of production and processing of those devices, and for subsequent shipping and handling up to the point of the catheter being withdrawn from the sheath by a health care provider at the point and time of final preparation for insertion into the vascular system of a patient.

BACKGROUND OF THE INVENTION

Intra-aortic balloon pumps (IABP) are used to provide counter pulsation within the aorta of ailing hearts over substantial periods of time, e.g. to provide ventricular assistance during cardiogenic shock, low cardiac output in post operative care, weaning from cardiopulmonary bypass, treatment for refractory unstable angina, and other circumstances of subnormal cardiac function. Such pumps include a large flexible intra-aortic balloon (IAB) which is readily inflatable under low pressure to substantial size and displacement. The balloon is mounted on a catheter device for insertion of the balloon into a remote artery, typically a femoral artery, and through the intervening vascular system of the patient to the aortic pumping site while the balloon is deflated and furled.

An intra-aortic balloon typically is a flexible balloon of substantial size, i.e. on the order of about 0.5" to about 1.0" in diameter when in an inflated but unstretched condition, and about 8" to 12" in length. Typical sizes are of 30 cc, 40 cc and 50 cc displacement. The balloon may be formed of any suitable material, with polyurethene presently being preferred. A hydrophilic coating preferably covers the balloon and forms a lubricous outer surface which is very slippery when wetted by an aqueous fluid, such as blood, while permitting processing and furling of the balloon and handling of the balloon and related pump mechanism in a normal manner when dry. Presently preferred coatings and appropriate modes of applying such coatings are disclosed in co-pending application No. 08/170,513, filed Dec. 20, 1993, the disclosure of which is incorporated herein by this reference.

The balloons are formed of thin films, as by a dip-casting process. One example is a polyether based polyurethene balloon of about 0.003"–0.005" wall thickness formed by dip-molding on an appropriately shaped mandrel, with later addition of a hydrophilic coating as referred to above. One presently preferred embodiment utilizes such balloons with wall thicknesses in the lower end of this range, i.e. 0.003"–0.004". It will be appreciated that the balloons are rather frail from a mechanical standpoint, and can be scratched or torn if not handled carefully and with appropriate safeguards during packaging, shipping and subsequent handling by the health care providers in the course of removal from the packaging in preparation for use.

In the course of manufacture, each balloon is assembled into a catheter assembly, with opposite ends of the balloon being bonded to the distal ends of two coaxial lumens. The balloon also is tightly furled about a distal portion of the inner lumen to facilitate subsequent insertion through a small opening into a patient's vascular system. The subassembly of the lumens and furled balloon then is threaded through a small packaging sheath, with the furled balloon thereby being drawn into the sheath which tightly surrounds the furled balloon section. The sheath remains on the balloon and maintains the balloon in its furled compaction to a minimum effective outside diameter during sterilization, packaging, shipping and handling, up to the place and time of insertion into the patient. While in its sheath, the furled balloon also typically is heated, e.g. to a temperature on the order of about 135° F. for about 12–16 hours, to assist in setting and thereby sustaining the furling during insertion following removal from the packaging sheath by the user.

Each sheath unit typically has been an extruded plastic tube, often with a substantial end-section affixed to one end of the tube as by being bonded or molded thereonto. The end section is of substantial size and body to provide a convenient means for gripping, handling and restraining the sheath unit against the forces of insertion and removal of the catheter balloon section. The end section also forms a graduated or flared inlet to assist in guiding the furled balloon section into the tube. The opposite or removal end of the tube often has been simply the square cut end formed during guillotine severance of the respective sheath tube from an indeterminate length of such tubing.

At the point of use, the balloon section is withdrawn from its packaging sheath by the health care user. It will be appreciated that this withdrawal may occur under conditions of stress and time urgency, by a wide variety of personnel.

In all events, it is desirable to provide a high degree of protection and assurance against scratching, abrasion or other damage to the balloon in the course of its insertion into and subsequent removal from the packaging sheath.

It is an object of this invention to provide improved packaging sheaths for intra-aortic balloon catheters.

It is a more specific object of this invention to provide such sheaths which reduce or avoid risks of scratching, abrasion or other damage to the balloon in the course of its insertion into the packaging sheath.

It is yet another object of this invention to provide such packaging sheaths of designs which reduce or avoid the risk of scratching, abrasion or other damage to the balloon in the course of its removal from the packaging sheath.

SUMMARY OF THE INVENTION

An intra-aortic balloon packaging sheath is provided which includes a long slim tube for storing a furled thin-walled intra-aortic balloon. The tube has a bore of uniform cross-section throughout its length. An entry section is molded onto one end of the tube, with the entry section including an outwardly flared entry port surface which is spaced from one end of the tube, and an internal passageway which is co-linear and congruent with the internal cross-section of the tube from the respective end of the tube through the intersection of the second internal passageway with the outwardly flared passageway. Thereby a smooth internal surface is provided through the flared passageway into the internal passageway and through the later into the tube.

In a preferred embodiment the tube is an extruded plastic tube and the entry section is a plastic molding of the same plastic whereby the molding of the end section onto the tube results in fusion bonding of the molded end section with the respective end portion of the sheath tube.

The opposite end of the sheath tube, which normally constitutes the catheter removal end, is inverted such that a distal end portion is turned outwardly and back circumjacent another portion of the tube wall to form a smoothly rounded exit passageway of the tube at this end. In the preferred embodiment, this end portion of the tubular passageway also is slightly flared.

These features provide smooth entry and exit sections, respectively, to minimize or avoid any risk of scratching, abrasion or other damage to the balloon in the course of its insertion into and subsequent removal from the packaging sheath.

Figure 1:
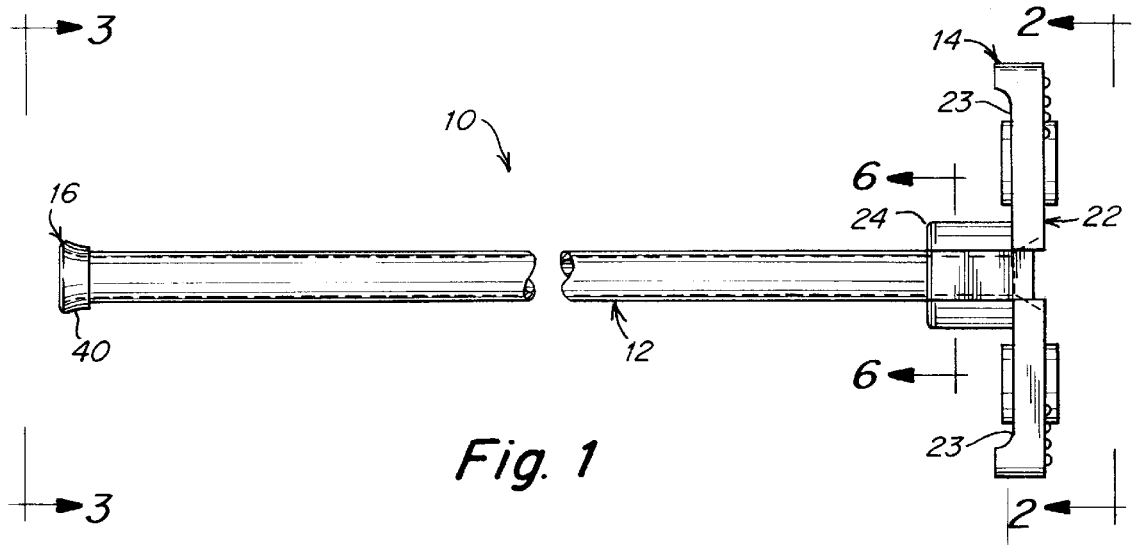
FIG. 1 is an enlarged side view of a packaging sheath for an intra-aortic balloon catheter, employing teachings of this invention.
Figure 2:
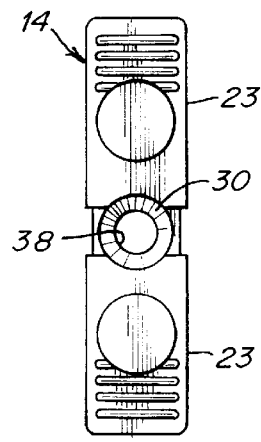
FIG. 2 is a right-end view of the device of FIG. 1, taken generally along line 2—2 and looking in the direction of the arrows.
Figure 3:
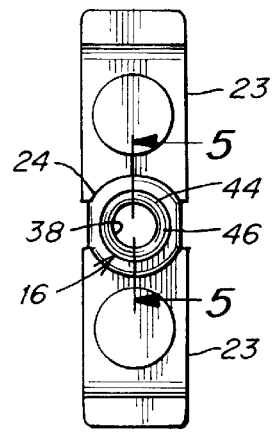
FIG. 3 is a left-end view of the device of FIG. 1, taken generally along line 3—3 of FIG. 1 and looking in the direction of the arrows.
Figure 4:
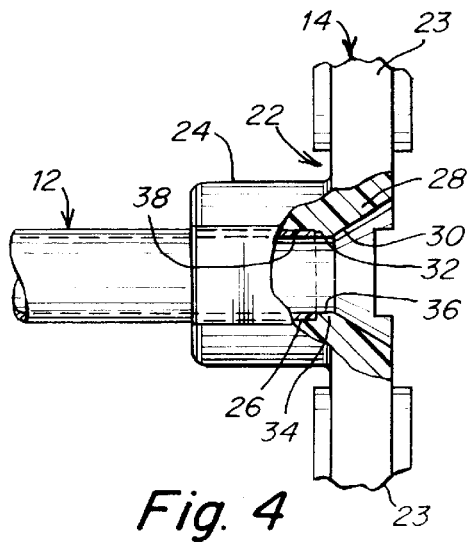
FIG. 4 is a somewhat enlarged side view, partially in section, illustrating the construction at the junction of the sheath tube and the end portion of the device in FIG. 1.
Figure 4A:
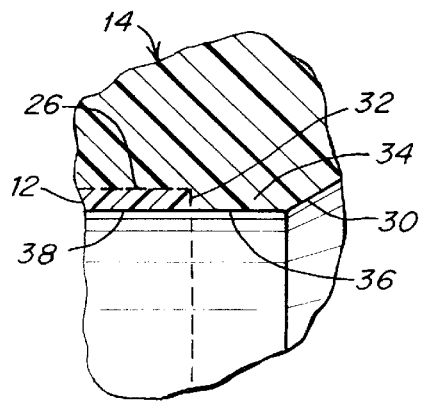
FIG. 4A is a further enlarged fragmentary sectional view corresponding to FIG. 4.

While the invention will be further described in connection with certain preferred embodiments, it is not intended to limit the invention to those embodiments. On the contrary, it is intended to cover all alternatives, modifications and equivalents as may be included within the spirit and scope of the invention.

DETAILED DESCRIPTION OF PREFERRED EMBODIMENTS

A packaging sheath unit 10 is illustrated which comprises an elongated sheath tube 12 with a T-shaped entrance end section 14 at one end. The opposite end portion of the tube, at its distal or exit end 16 is reformed by being inverted outwardly and back upon itself, as will be referred to further below.

The tube 12 is a small circular cylindrical tube, typically being cut from an indeterminate length of extruded plastic tubing. The entrance section 14 includes a center portion 22 which is in co-axial surrounding relationship to the respective end portion of the tube 12 and the axial extension of its inner cylindrical bore, and a pair of oppositely disposed wing portions 23. The wing portions extend outward from the center portion 22, forming a T-shape therewith.

The section 22 includes a collar portion 24, a guide portion 28 and an intervening portion 34. The collar portion 24 surrounds and is bonded to the adjacent end portion 26 of the tube. The guide portion 28 defines a truncated conical or funnel shaped smooth interior guide surface 30 which is spaced from and coaxially aligned with the distal end 32 of the tube 12. The intervening portion 34 defines a circular cylindrical surface 36 which is co-axial and congruent with the inner bore surface 38 of the end portion 26 of the tube 12 and extends outward to an intersection with the surface 30. The surfaces 30, 36, 38 form a smooth continuous series of surfaces comprising the funnel shaped entrance, the intervening portion and the inner bore of the tube, without any sharp edges, shoulders, cut-edges, burrs or roughness. This provides a smooth continuum of surfaces from the entrance end of the guide 30 into the tube 12 for insertion of the balloon section of the catheter into the sheath unit 10 with little or no risk of abrasion, scratching or tearing of the material of the balloon, even where the furled balloon has a snug compacting fit in the bore 38.

The end section 14 also provides a convenient gripping area or handle for manipulating and securing the sheath unit during insertion of the catheter assembly into the tube 12, and subsequently withdrawing the catheter unit therefrom. The end section 14 also is useful for securing and retaining the sheath unit in an appropriate cavity of a shipping tray both during shipping and while the catheter assembly is withdrawn therefrom, in the recommended mode of removal of the catheter units at the point of use. Thus, while the illustrated configuration of the external portions is a T-shape corresponding generally to catheter sheaths used heretofore by the Cardiac Assist Division of St. Jude Medical, Inc., it will be appreciated that any of a variety of configurations may be employed.

Figure 5:
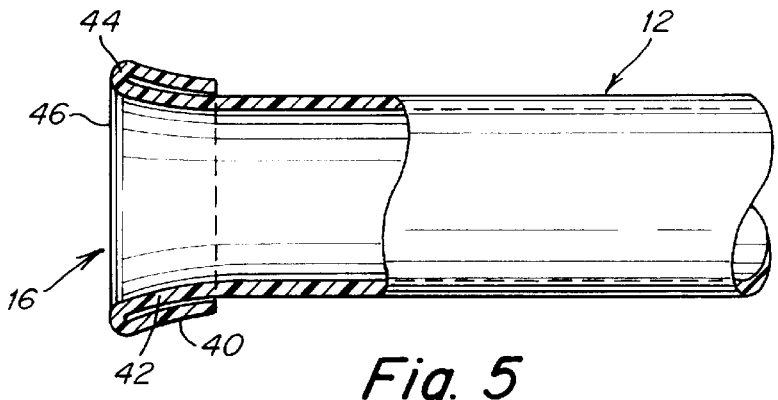
FIG. 5 is an enlarged side view of the catheter removal end of the device of FIG. 1, taken partially in section along an axial diametral plane as indicated by line 5—5 of FIG. 3.
Figure 6:
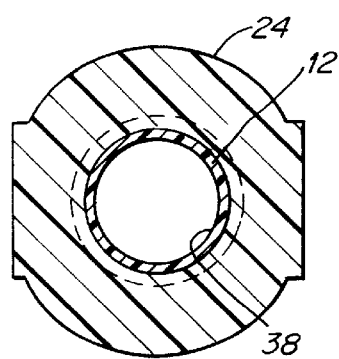
FIG. 6 is a sectional view taken generally along line 6—6 of FIG. 1.

Referring particularly to FIG. 5, at the distal end 16 a short end portion 40 of the tube wall is inverted over the adjacent portion 42 to lie circumjacent thereto, forming an intervening annular fold or bight 44 and thereby readily forming a smoothly rounded annular exit surface 46 from the bore of the tube 12. The resulting exit surface avoids exposure of the balloon to any cut edges, other sharp corners or roughness as a balloon catheter section is withdrawn through this end of the sheath, even if the withdrawal is not directly co-axial but is at some angle of deflection in any direction relative to the extended axis of the tube 12.

Figure 7:
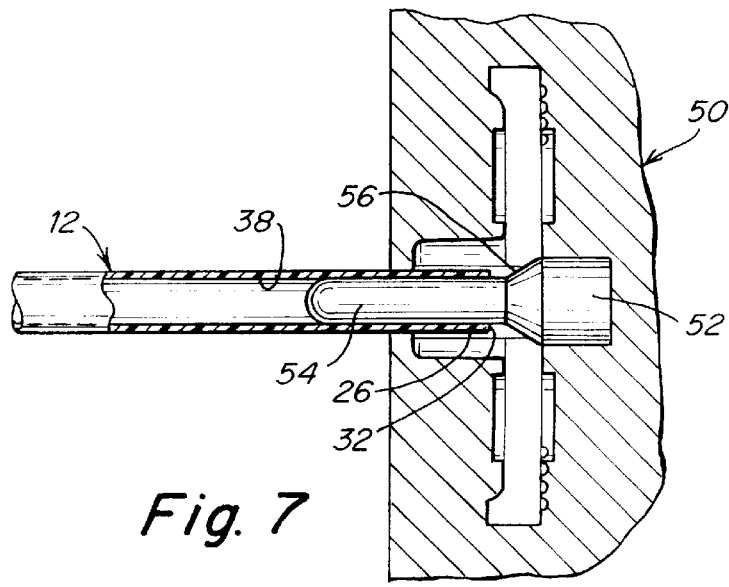
FIG. 7 illustrates the positioning of a core pin and injection mold relative to a sheath tube for forming an end entrance and related entry passageway configuration of the device of FIG. 1.

A preferred manner of forming the entrance section 14 by injection molding is illustrated schematically in FIG. 7. The respective end portion 26 of the tube 12 extends into an appropriate cavity of an injection mold 50. A core pin 52 includes a cylindrical smooth surfaced extension 54 which preferably is slightly oversize relative to bore 38 to provide a slight interference fit within the bore of the tube 12. The core pin 52 also includes a smooth-walled truncated conical section 56 for forming the entrance guide surface 30. It will be observed that the tube 12 is positioned such that its proximal end 32 is spaced a significant distance from the conical surface 56, for the formation of the transition section 34 and related smooth inner surface 36 therebetween. An appropriate molding material is injected into the cavity in a known manner to form the end section 14.

The material to be molded for forming the section 14 should be compatible with the material of the tube 12, such as to effect a good bond therebetween. In the preferred embodiment both the tube and the injection molding material are high density polyethylene to insure compatibility and substantially the same melting temperatures, e.g. 380–450° F. range, or about 420° F. It is believed that the use of corresponding materials results in partial melting of the mating annular and end surfaces of the tube 12 in the course of the injection molding of the end section, thereby providing a melt/merge fusion bond at these interfaces and particularly at and along the interface of end 32, which further assures the formation of a unified continuum of surfaces from the tapered guide surface 30 into the bore of the tube 12. Accordingly, the drawings sometimes show the interfaces between the sheath tube and the molded-on end section in dashed lines.

By way of further example, for packaging an 8 Fr IABC the tubing 12 is an extruded high density polyethylene tube having an ID of about 0.120", an OD of about 0.133" and a wall thickness of about 0.065". The collar section is about 0.250" in length overall, which includes a transition surface section 36 about 0.025" long, and a conical entrance 30 with an included angle of about 60°. The main body of each wing is about 0.310" wide and 0.098" thick, and the two wings 23 have a total span of about 1.19".

Figure 8:
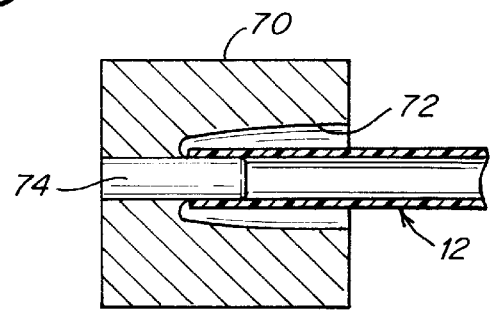
FIG. 8 is a sectional view showing the distal end of the sheath tube mounted on a heated tipping die for reforming this end of the sheath tube.
Figure 9:
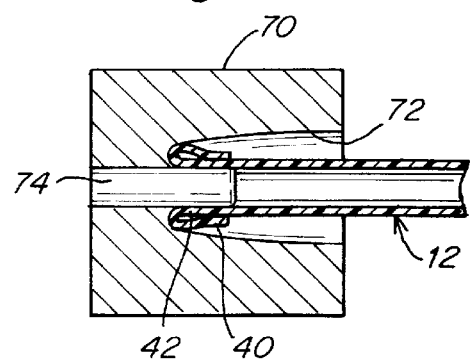
FIG. 9 is a view corresponding to FIG. 8, showing the distal end being reformed by inversion.

The inverted configuration of the distal end 16 may be provided by any suitable technique. A currently preferred method is a hot die forming process as illustrated generally in FIGS. 8 and 9. A die block 70 is formed with an appropriate generally U-shaped recess 72 to receive one end of the tube 12. A die pin 74 extends co-axially into the cavity 72 and is of a size to fit snugly within the bore of the tube 12. The pin 74, and adjacent portions of the block 70 if and as necessary, are heated by any appropriate means to a temperature sufficient to soften the material of the inserted end portion of the tube 12 such that axial pressure causes the distal tube portion 40 to be progressively inverted over the next adjacent tube portion 42, as illustrated. That is, the end portion 40 is progressively enlarged in diameter and turned back in circumjacent relation to the next succeeding portion 42 of the tube. The result is a rounded, smooth annular exit surface 46 formed by reverse bending and rolling back the end portion 40 of the tube 12. Any sharp edges, burrs or roughness that may have been formed at the distal end of the tube 12 during its formation are removed from the area of contact with the balloon during withdrawal. The pin 74 and cavity 72 may be of a configuration to also provide a slight outward taper or flare in the exit end of the sheath tube, as illustrated in FIG. 5.

It will be appreciated that improved packaging sheaths for the balloon portion of intra-aortic balloon catheters have been provided which meet the objects of this invention.

The invention has been described in considerable detail with reference to certain embodiments, and particularly with respect to the preferred embodiments thereof. However, it will be understood that variations, modifications and improvements may be made, particularly by those skilled in this art and in light of the teachings referred to herein within the spirit and scope of the invention as claimed.

What is claimed is:

1. A method of forming an intra-aortic balloon packaging sheath, comprising steps of:

providing an extruded plastic packaging sheath tube having an internal bore therethrough which is constructed and arranged for storing a furled, intra-aortic balloon section of a catheter;

partially inserting a core pin into the bore at a first end portion of the sheath tube, the core pin being configured with an extension having a size corresponding to the bore of the tube and a flared section extending outwardly from an end of the extension, the extension being partially inserted into the bore so that the first end portion of the tube is spaced from the flared section of the core pin to expose a portion of the extension protruding from the bore at the first end portion of the tube; and insert molding an entrance guide onto the first end portion of the tube by injecting a plastic into a mold and in contact with the exposed portion and the flared section of the core pin and an external surface of the first end portion of the tube to form a smooth-walled entrance passageway for guiding the furled intra-aortic balloon into the internal bore of the tube, the entrance passageway including a flared outer portion formed by the flared section of the core pin and a smooth walled transition from the flared outer portion into the tube bore formed by the exposed portion of the extension.

2. The method recited in claim 1, wherein the plastic injected into the mold and the tube have substantially the same melting temperature.

3. The method recited in claim 2, wherein the plastic injected into the mold is of essentially the same composition as the extruded plastic tube.

4. The method recited in claim 3, wherein the plastic injected into the mold and the tube are formed of high density polyethylene.

5. The method recited in claim 1, wherein molding the entrance guide includes forming the flared outer portion with a truncated conical surface and the transition with a cylindrical surface by configuring the core pin with a conically-shaped flared section and a cylindrically-shaped extension.

6. The method recited in claim 1, wherein molding the entrance guide includes forming the flared outer portion and the transition of the entrance passageway in axial alignment with the internal bore of the sheath tube.

7. The method recited in claim 1, further comprising forming a second end portion of the sheath tube with a smoothly rounded opening to facilitate removal of the intra-aortic balloon section of the catheter from the internal bore of the sheath tube.

8. The method recited in claim 7, wherein forming the rounded opening at the second end portion includes inverting a first segment of the tube to lie circumjacent an adjacent second segment of the tube.

9. The method recited in claim 8, wherein inverting the first segment includes applying an axial pressure between the tube and a die block having a recess therein that is configured to receive and shape the second end portion of the tube.

10. The method recited in claim 9, wherein inverting the first segment includes inserting a die pin into the bore at the second end portion of the tube.

11. The method recited in claim 10, wherein forming the rounded opening includes heating portions of the die block and the die pin to a temperature sufficient to soften the second end portion of the tube.

12. The method recited in claim 10, further comprising configuring the recess in the die block and the die pin to form the second end portion with an outward taper.

* * * * *